United States Patent
Everaert et al.

(10) Patent No.: US 11,154,475 B2
(45) Date of Patent: *Oct. 26, 2021

(54) METHOD FOR COLORING OR BLEACHING HAIR FIBERS

(71) Applicant: HERCULES LLC, Wilmington, DE (US)

(72) Inventors: Emmanuel Paul Jos Marie Everaert, Galder (NL); Gijsbert Kroon, Giessenburg (NL); Thi Diem Truc Tran, Hendrik Ido Ambacht (NL)

(73) Assignee: HERCULES LLC, Wilmington, DE (US)

( * ) Notice: Subject to any disclaimer, the term of this patent is extended or adjusted under 35 U.S.C. 154(b) by 659 days.

This patent is subject to a terminal disclaimer.

(21) Appl. No.: 15/864,559

(22) Filed: Jan. 8, 2018

(65) Prior Publication Data

US 2018/0193242 A1 Jul. 12, 2018

Related U.S. Application Data

(60) Provisional application No. 62/444,253, filed on Jan. 9, 2017.

(51) Int. Cl.
| | | |
|---|---|---|
| *A61Q 5/08* | (2006.01) | |
| *A61Q 5/10* | (2006.01) | |
| *A61K 8/42* | (2006.01) | |
| *A61K 8/41* | (2006.01) | |
| *A61K 8/36* | (2006.01) | |
| *A61K 8/60* | (2006.01) | |

(52) U.S. Cl.
CPC .................. *A61K 8/42* (2013.01); *A61K 8/36* (2013.01); *A61K 8/416* (2013.01); *A61K 8/60* (2013.01); *A61Q 5/08* (2013.01); *A61Q 5/10* (2013.01); *A61K 2800/4324* (2013.01); *A61K 2800/884* (2013.01)

(58) Field of Classification Search
None
See application file for complete search history.

(56) References Cited

U.S. PATENT DOCUMENTS

| | | |
|---|---|---|
| 5,224,964 A | 7/1993 | Shami |
| 6,540,791 B1 | 4/2003 | Dias |
| 7,204,861 B2 | 4/2007 | Marsh et al. |
| 9,095,518 B2 | 8/2015 | Pressly et al. |
| 9,144,537 B1 | 9/2015 | Pressly et al. |
| 9,326,926 B2 | 5/2016 | Pressly et al. |
| 10,568,823 B2 * | 2/2020 | Everaert ............... A61K 8/498 |
| 2004/0105830 A1 | 6/2004 | Boswell et al. |
| 2006/0064824 A1 | 3/2006 | Godfrey |
| 2015/0034117 A1 | 2/2015 | Pressly et al. |
| 2015/0034119 A1 | 2/2015 | Pressly et al. |
| 2016/0081899 A1 | 3/2016 | Pressly et al. |

OTHER PUBLICATIONS

Instrumental Analysis of the Human Hair Damaged; Journal of Fashion Business, vol. 12, No. 6.

* cited by examiner

*Primary Examiner* — Jyothsna A Venkat

(74) *Attorney, Agent, or Firm* — William J. Davis; Nathalie Tietcheu

(57) ABSTRACT

Disclosed is a method for coloring or bleaching a hair comprising steps of: (a) applying a first formulation comprising a hair coloring agent or bleaching agent in the hair and (b) applying to the hair a second formulation comprising a hair composition of an amide and/or an alkyl ammonium carboxylate salt. The amide can be a monoamide and/or a bisamide.

9 Claims, 1 Drawing Sheet

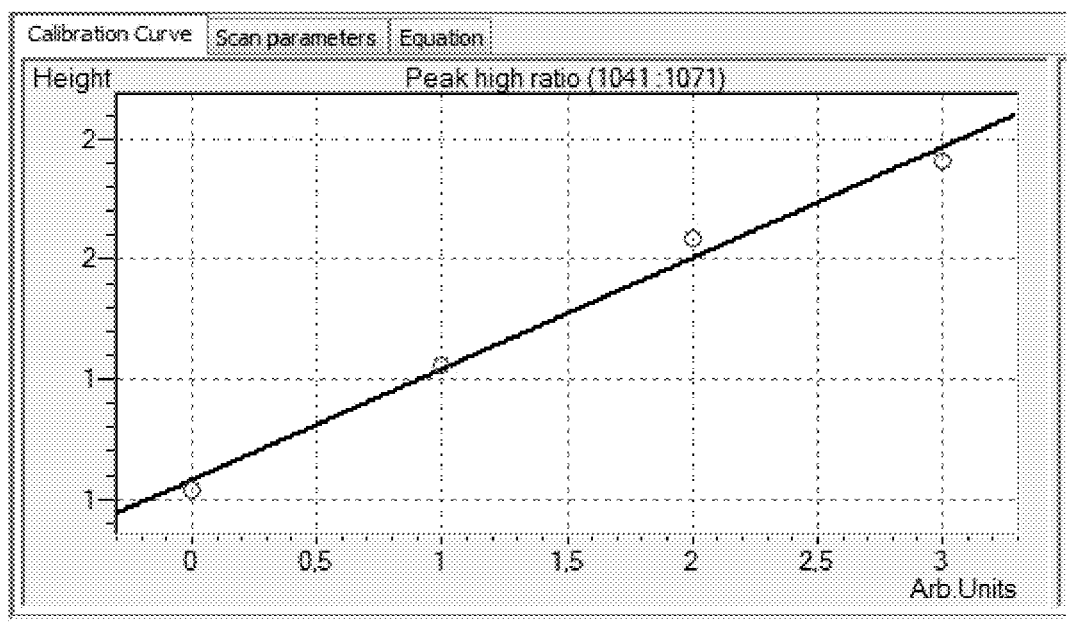

METHOD FOR COLORING OR BLEACHING HAIR FIBERS

CROSS REFERENCE TO RELATED APPLICATIONS

The present application claims the benefit under 35 U.S.C. 119 (e) of U.S. Provisional Patent Application Ser. No. 62/444,253, filed on Jan. 9, 2017, the entire content of which is hereby expressly incorporated herein by reference.

BACKGROUND OF THE INVENTION

1. Field of the Disclosed and Claimed Inventive Concepts

The presently disclosed and/or claimed inventive process(es), procedure(s), method(s), product(s), result(s), and/or concept(s) (collectively hereinafter referred to as the "present disclosure") relates generally to a method for coloring or bleaching a hair comprising steps of: (a) applying a first formulation comprising a hair coloring agent or bleaching agent to the hair and (b) applying to the hair a second formulation comprising a hair composition of an amide and/or an alkyl ammonium carboxylate salt.

2. Background

The coloring and/or bleaching of hair has become increasingly popular in recent years. However, fading of artificial hair color has become a widespread problem and a frequent complaint by consumers. Fading can occur during shampoo washing treatment as color wash-out, or can be initiated by environmental circumstances, such as by exposure to UV radiation. The washing process is the most significant factor in the removal of hair color, while UV exposure has a significant impact only after 90 hours of intense irradiation. Furthermore, the surfactants present in shampoo formulations provide a wetting function which brings moisture into the hair shaft, thus facilitating the removal of the dye molecules to exit during the water rinsing process. Maintaining hair color and minimizing hair color fading is highly desirable in the hair care market.

The coloring and/or bleaching formulations also cause severe hair damage, especially when coloring/bleaching treatments are repeated. Moreover, various standard daily actions to the hair, for example hair brushing, hair blow-drying, and sun light exposure can cause even more damage to the hair. Similar damage to the hair can also result from permanent wave treatments. In both coloring and permanent wave processes, improvements are also needed to repair damage and/or to strengthen the hair during or after such styling treatments.

There is a need for hair coloring and/or bleaching formulations and treatments that can enhance color intensity, reduce and repair hair damage and/or strengthen keratin in hair damaged from coloring and/or bleaching treatments.

BRIEF DESCRIPTION OF THE FIGURES

FIG. 1 shows a calibration curve of peak height ratios of 1041 $cm^{-1}$/1076 $cm^{-1}$ for zero, once, twice and three times bleached hair versus the corresponding bleaching times.

DETAILED DESCRIPTION OF THE INVENTIVE CONCEPT(S)

Before explaining at least one embodiment of the present disclosure in detail, it is to be understood that the present disclosure is not limited in its application to the details of construction and the arrangement of the components or steps or methodologies set forth in the following description or illustrated in the drawings. The present disclosure is capable of other embodiments or of being practiced or carried out in various ways. Also, it is to be understood that the phraseology and terminology employed herein is for the purpose of description and should not be regarded as limiting.

Unless otherwise defined herein, technical terms used in connection with the present disclosure shall have the meanings that are commonly understood by those of ordinary skill in the art. Further, unless otherwise required by context, singular terms shall include pluralities and plural terms shall include the singular.

All patents, published patent applications, and non-patent publications mentioned in the specification are indicative of the level of skill of those skilled in the art to which the present disclosure pertains. All patents, published patent applications, and non-patent publications referenced in any portion of this application are herein expressly incorporated by reference in their entirety to the same extent as if each individual patent or publication was specifically and individually indicated to be incorporated by reference.

All of the compositions and/or methods disclosed herein can be made and executed without undue experimentation in light of the present disclosure. While the compositions and methods of the present disclosure have been described in terms of preferred embodiments, it will be apparent to those of ordinary skill in the art that variations may be applied to the compositions and/or methods and in the steps or in the sequence of steps of the method described herein without departing from the concept, spirit and scope of the presently disclosed and/or claimed inventive concept(s). All such similar substitutes and modifications apparent to those skilled in the art are deemed to be within the spirit, scope and concept of the present disclosure.

As utilized in accordance with the present disclosure, the following terms, unless otherwise indicated, shall be understood to have the following meanings.

The use of the word "a" or "an" when used in conjunction with the term "comprising" may mean "one," but it is also consistent with the meaning of "one or more," "at least one," and "one or more than one." The use of the term "or" is used to mean "and/or" unless explicitly indicated to refer to alternatives only if the alternatives are mutually exclusive, although the disclosure supports a definition that refers to only alternatives and "and/or." Throughout this application, the term "about" is used to indicate that a value includes the inherent variation of error for the quantifying device, the method being employed to determine the value, or the variation that exists among the study subjects. For example, but not by way of limitation, when the term "about" is utilized, the designated value may vary by plus or minus twelve percent, or eleven percent, or ten percent, or nine percent, or eight percent, or seven percent, or six percent, or five percent, or four percent, or three percent, or two percent, or one percent. The use of the term "at least one" will be understood to include one as well as any quantity more than one, including but not limited to, 1, 2, 3, 4, 5, 10, 15, 20, 30, 40, 50, 100, etc. The term "at least one" may extend up to 100 or 1000 or more depending on the term to which it is attached. In addition, the quantities of 100/1000 are not to be considered limiting as lower or higher limits may also produce satisfactory results. In addition, the use of the term "at least one of X, Y, and Z" will be understood to include X alone, Y alone, and Z alone, as well as any combination of X, Y, and Z. The use of ordinal number terminology (i.e., "first", "second", "third", "fourth", etc.) is solely for the purpose of differentiating between two or more items and, unless otherwise stated, is not meant to imply any sequence or order or importance to one item over another or any order of addition.

As used herein, the words "comprising" (and any form of comprising, such as "comprise" and "comprises"), "having" (and any form of having, such as "have" and "has"), "including" (and any form of including, such as "includes" and "include") or "containing" (and any form of containing, such as "contains" and "contain") are inclusive or open-ended and do not exclude additional, unrecited elements or method steps. The term "or combinations thereof" as used herein refers to all permutations and combinations of the listed items preceding the term. For example, "A, B, C, or combinations thereof" is intended to include at least one of: A, B, C, AB, AC, BC, or ABC and, if order is important in a particular context, also BA, CA, CB, CBA, BCA, ACB, BAC, or CAB. Continuing with this example, expressly included are combinations that contain repeats of one or more item or term, such as BB, AAA, MB, BBC, AAABCCCC, CBBAAA, CABABB, and so forth. The skilled artisan will understand that typically there is no limit on the number of items or terms in any combination, unless otherwise apparent from the context.

As used herein the term "hair" or "hair fiber(s)" to be treated may be "living" i.e. on a living body or may be "non-living" i.e. in a wig, hairpiece or other aggregation of nonliving keratinous fibers. Mammalian, human hair is preferred. However, wool, fur and other keratin containing fibers are suitable substrates for the compositions according to the present disclosure. "Hair" and "hair fiber(s) are used interchangeably in the present disclosure.

"Virgin hair" means hair that has never been treated chemically and/or echanically including but not limited to coloring, bleaching, relaxing, straightening, perming, grooming, and exposures to sun, UV light, salty water, heat appliance, etc.

The term "coloring hair" in accordance with the present disclosure means hair which has been colored with a permanent, semi-permanent or temporary artificial color, which can be different from the original color of the hair.

The term "bleaching hair" in accordance with the present disclosure means permanent lightening of hair by a bleaching process, which causes permanent lightening of the melanin pigments found in the hair.

As used herein, the terms "pharmaceutically acceptable" and "cosmetically acceptable" are used interchangeably and refer to those compounds, materials, and/or formulations, which are, within the scope of sound medical judgment, suitable for use in contact with the tissues of human beings and animals without excessive toxicity, irritation, allergic response, or other problems or complications commensurate with a reasonable benefit/risk ratio. More specifically, pharmaceutically acceptable refers to a material, compound, or formulation that is suitable fair use in contact with the skin, scalp, or hair. Pharmaceutically acceptable materials are known to those of ordinary skill in the art.

The present disclosure relates generally to a method for coloring or bleaching a hair comprising steps of: (a) applying a first formulation comprising a hair coloring agent or bleaching agent to the hair; and (b) applying to the hair a second formulation comprising a hair composition comprising an amide and/or an alkyl ammonium carboxylate salt. The amide can be a monoamide and/or a bisamide.

In one aspect, the steps (a) and (b) of the method can be performed simultaneously. In one non-limiting embodiment, the first and the second formulations can be mixed together at the time of use and prior to the application.

In another aspect, the steps (a) and (b) of the method can be performed sequentially with the step (a) performed prior to the step (b).

There are various systems for coloring hair. Temporary hair colorings are those which last generally until the first shampoo. The colors employed, often referred to as fugitive colors, are typically of a higher molecular weight and are incapable of penetrating the cortex of the hair and consequently are externally deposited on the hair. Temporary hair dyes generally include basic dyes, acid dyes, disperse dyes, pigments or metallized dyes, belonging to various chemical classes including azo, anthraquinone, triphenylmethane, phenazinic, xanthenic, and benzoqumoneimine.

Semi-permanent hair coloring is resistant to several shampooing. The colors employed are typically direct dyes of low molecular weight and capable of penetrating the cortex of the hair. Semi-permanent hair colorings belong generally to the chemical classes of nitrophenylenediamines, nitroaminophenols and aminoanthraquinones.

Permanent hair colorings are those that are resistant to shampooing, brushing, friction, light, etc. The oxidation dyes, or para-dyes, used in the permanent hair colorings are colorless until oxidized by an oxidizing agent, typically hydrogen peroxide or a derivative.

The hair coloring agents can include but are not limited to oxidative dyeing compositions. Such compositions comprise oxidative hair dye precursors also known as primary intermediates and couplers that will deliver a variety of hair colors to the hair. These small molecules are activated by the oxidizing agent and further react with molecules to form a larger colored complex in the hair shaft.

These compositions are well known in the art, and can include, but are not limited to, aromatic diamines, aminophenols, aromaticdiols and their derivatives. A representative but not exhaustive list of oxidation dye precursor can be found in Sagarin, "Cosmetic Science and Technology", "Interscience, Special Edn. Vol. 2 pages 308 to 310, which is herein incorporated in its entirety by reference. The hair coloring agent may also include non-oxidative hair dyes. i.e. direct dyes which may be used alone or in combination with the above described oxidative dyes. Suitable direct dyes can include azo or anthraquinone dyes and nitro derivatives of the benzene series and/or melanin precursors and mixtures thereof.

The hair coloring agent can generally comprise from about 0.001% to about 10% by weight of dyes. For example, the coloring agent providing low intensity dyeing such as natural blonde to light brown hair shades generally comprise from about 0.001% to about 5%, or from about 0.1% to about 2%, or from about 0.2% to about 1% by weight of dyeing composition of precursors and couplers. Darker shades such as browns and black typically comprise from 0.001% to about 10% by weight, or from about 0.05% to about 7% by weight, or from about 1% to about 5% of precursors and couplers.

In addition to acting as an oxidizing agent, hydrogen peroxide is also important ability to solubilize the natural melanin pigments of the hair, consequently bleaching or lightening the hair. Thus, hair can be lightened, for example, to provide a blonde shade by employing hydrogen peroxide to first remove natural pigments, and then to impart a new color to the lightened hair with oxidation dyes. Typically, a combined bleach and oxidation dye will be employed to bleach the hair while the dyes are penetrating. This method allows dark hair to be lightened by several shades while giving the appearance of not having been bleached.

Hydrogen peroxide has also been employed in combination with a 1:2 chromium complex of a mono azo dye and in combination with a dye derived from triarylmethane to lighten and tint hair. These types of dyes are generally classed as temporary hair dyes as discussed previously.

Any type of pigment type coloring agent can be employed in the practice of the present disclosure, either organic or inorganic, including but not limited to pigments such as, raw sienna, burnt sienna, red sienna, ultramarine blue, yellow, brown or red ocher, cobalt blue, umber, and organic pigments, either synthetic or natural, such as the pigments contained in the groups chlorophylls, carotenoids, and flavanoids.

Especially effective as permanent hair colorants as used in the present disclosure are tempera paints, e.g., watercolor paints consisting of pigment ground in water and mixed with egg yolk. These are the paints typically used as finger paints. An especially effective tempera paint for use as a permanent hair colorant as used in the present disclosure are acrylic type tempera paints, typically used by artists in silk-screening. Permanent as used in the present disclosure means more permanent or longer lasting than the results obtainable by so-called permanent oxidation dyes.

Tempera paints, generally, are emulsions comprising pigments ground in a medium miscible with water. The emulsions-comprise an oily ingredient such as oil, wax or resin, and an aqueous, thick gummy or glue-like ingredient.

The bleaching agent used in the present disclosure can encompass compositions containing combinations herein of: (a) at least one oxidizing agent; (b) a buffering system comprising at least one pH modifying ingredient selected from the group consisting of (i) borates buffers, (ii) alkalizing agents, and mixtures thereof; (c) at least one stabilizer; and (d) at least one hair care ingredient selected from the group consisting of (i) surfactants, (ii) catalysts, (iii) thickeners, (iv) conditioners, and mixtures thereof. Moreover, other complex compositions which may or may not be active ingredients can also be included. Thus, the term "hair bleaching agent" and also the term "hair coloring agent" are intended to apply to compositions which contain additional ingredient commonly known and used in hair bleaching and coloring compositions as viscosity modifiers, conditioning enhancers, preservatives, perfumes, and ingredients used to modify aesthetics.

It is known that bleaching agents act on part of the melanin in the hair to oxidize it, thus solubilizing a portion of the melanin in the hair and consequently lightening the natural hair color. A bleaching agent as used here means any agent capable of acting to physically or chemically remove the color causing compounds contained in the hair to cause the hair color to become lighter, including but not limited to hydrogen peroxide, an admixture of hydrogen peroxide and hair bleaching powder, or any other commercially available hair bleach products.

In the present disclosure, hydrogen peroxide can be employed as a main hair lightening constituent. Hydrogen peroxide can be employed by itself in lightening hair color. In the present disclosure, hydrogen peroxide can also be combined with commercially available hair bleaching powders. The hair bleaching powders allow hydrogen peroxide to be applied to the hair in a more controlled manner. For example, the hair bleaching powders can be mixed with hydrogen peroxide in various ratios to make a paste having different strengths of hydrogen peroxide, consequently providing various bleaching or hair lightening rates. If desired, a conditioning agent can be incorporated into the paste, for example, milk, beer or olive oil, to help counteract damaging effects of hydrogen peroxide.

In addition to hydrogen peroxide, other water-soluble peroxygen oxidizing agents can be used in the present disclosure. "Water-soluble" as defined herein means that in standard condition at least 0.1 g, or 1 g, or 10 g of the oxidizing agent can be dissolved in 1 liter of deionized water. The oxidizing agents are valuable for the initial solubilization and decolonization of the melanin (bleaching) and accelerate the oxidation of the oxidative dye precursors (oxidative dyeing) in the hair shaft.

The water-soluble oxidizing agents used in the present disclosure can include inorganic peroxygen materials capable of yielding hydrogen peroxide in an aqueous solution. The inorganic peroxygen can include, but are not limited to, inorganic alkali metal peroxides such as sodium periodate and sodium peroxide. In addition, organic peroxides such as urea peroxide, melamine peroxide, and inorganic perhydrate salt bleaching compounds, such as alkali metal salts of perborates, percarbonates, perphosphates, persilicates, persulphates and the like can also be used in the present disclosure. These inorganic perhydrate salts may be incorporated as monohydrates, tetrahydrates etc. Alkyl and aryl peroxides, and or peroxidases may also be used.

Mixtures of two or more such oxidizing agents can also be used if desired. The oxidizing agents may be provided in an aqueous solution or as a powder which is dissolved prior to use. In one non-limiting embodiment, according to the present disclosure, the oxidizing agents can be hydrogen peroxide, percarbonate, persulphates and their combinations thereof. The hair coloring or bleaching agent comprises from about 0.1% to about 15% by weight, or from about 1% to about 10% by weight, or from about 2% to about 7% by weight of an oxidizing agent.

Another oxidizing agent for use herein is a source of peroxymonocarbonate ions. Such a source can be formed in situ from a source of hydrogen peroxide and a hydrogen carbonate ion source. Such an oxidizing agent has been found to be particularly effective at a pH of up to about 9.5, or from 7.5 to 9.5, or from 8.4 to 9.5, or up to about 9. Moreover, this system is also particularly effective in combination with a source of ammonia or ammonium ions. It has been found that this oxidizing agent can deliver improvements to the desired hair color results particularly with regard to the delivery of high lift, whilst considerably reducing the odor, skin and scalp irritation and damage to the hair fibers.

Accordingly, any source of these ions may be utilized. Suitable sources for use herein can include sodium, potassium, guanidine, arginine, lithium, calcium, magnesium, barium, ammonium salts of carbonate, carbamate and hydrocarbonate ions and mixtures thereof such as sodium carbonate, sodium hydrogen carbonate, potassium carbonate, potassium hydrogen carbonate, guanidine carbonate, guanidine hydrogen carbonate, lithium carbonate, calcium carbonate, magnesium carbonate, barium carbonate, ammonium carbonate, ammonium hydrogen carbonate and mixtures thereof. Percarbonate salts may also be utilized to provide both the source of carbonate ions and oxidizing agent. The sources of carbonate ions, carbamate and hydrocarbonate ions can be sodium hydrogen carbonate, potassium hydrogen carbonate, ammonium carbamate, and mixtures thereof.

The hair coloring or bleaching agent comprises from about 0.1% to about 15% by weight, or from about 1% to about 10% by weight, or from about 1% to about 8% by weight of a hydrogen carbonate ion and from about 0.1% to about 10% by weight, or from about 1% to about 7% by weight, or from about 2% to about 5% by weight of a source of hydrogen peroxide.

The hair coloring or bleaching agent may further comprise additional ingredients which can include, but are not limited to, alkalizing agents, surfactants, thickeners and/or rheology modifiers, pacifiers such as mica, solvents, enzymes, surfactants, conditioning agents, carriers, antioxidants, stabilizers, chelants, penning actives, perfume, reducing agents, hair swelling agents and/or polymers.

In particular, the hair coloring or bleaching agent may optionally comprise at least one source of alkalizing agent, for example, a source of ammonium ions and or ammonia. In one non-limiting embodiment, the alkalizing agents are those which provide a source of ammonium ions. Any source of ammonium ions is suitable for use herein. Examples of the sources can include, but are not limited to, ammonium chloride, ammonium sulfate, ammonium nitrate, ammonium phosphate, ammonium acetate, ammonium carbonate, ammonium hydrogen carbonate, ammonium carbamate, ammonium hydroxide, percarbonate salts, ammonia and mixtures thereof. The ammonium salts can be ammonium carbonate, ammonium hydrogen carbonate, ammonium carbamate, ammonia and mixtures thereof. The compositions of the present disclosure may comprise from about 0.1% to about 10% by weight, or from about 0.5% to about 5%, or from about 1% to about 3% of an alkalizing agent. The ammonium ions and carbonate ions can be present in the agent at a weight ratio of from 3:1 to 1:10, or from 2:1 to 1:5.

The hair coloring and/or bleaching agent can have a pH of m about 11 to about 7, or from about 9.5 to about 7.5, or from about 9.5 to about 8.4, or about 9.4 to about 8.5 or at about pH 9.0.

The hair coloring or bleaching agent may also comprise a source of radical scavenger. As used herein the term radical scavenger refers to a species that can react with a radical, for example carbonate radical to convert radical by a series of fast reactions to a less reactive species.

In one non-limiting embodiment, the hair composition of an amide and/or an alkyl ammonium carboxylate salt can be represented by Formula (I), or Formula (II), or Formula (I) and Formula (II).

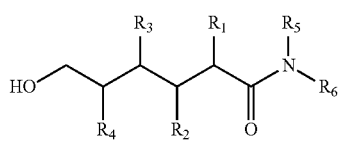

Formula (I)

wherein $R_1$-$R_4$ are independently hydrogen, a hydrocarbon radical having 1 to about 10 carbon atoms, a hydroxyl group, an amino group, a sulfhydryl group, an aryl group, or a halogen; and $R_5$ and $R_6$ are independently hydrogen, an aliphatic hydrocarbon group, an alicyclic hydrocarbon group, an aryl group, an alkylaryl group, or a heterocyclic group. The aliphatic hydrocarbon group, the alicyclic hydrocarbon group, the aryl group, the alkylaryl group, or the heterocyclic group can be substituted with at least one hydroxyl group.

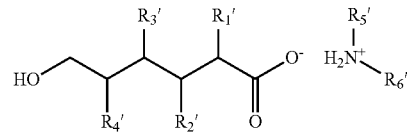

Formula (II)

wherein $R'_1$-$R'_4$ are independently hydrogen, a hydrocarbon radical having 1 to about 10 carbon atoms, a hydroxyl group, an amino group, a sulfhydryl group, an aryl group, an alkylaryl group or a halogen; and $R'_5$ and $R'_6$ are independently hydrogen, an aliphatic hydrocarbon group, an alicyclic hydrocarbon group, an aryl group, an alkylaryl group, or a heterocyclic group, excluding $R'_5$ and $R'_6$ being simultaneous hydrogens. The aliphatic hydrocarbon group, the alicyclic hydrocarbon group, the aryl group, the alkylaryl group or the heterocyclic group can be substituted with at least one hydroxyl group.

The amounts of Formula (I) and Formula (II) can be varied when the hair composition comprises Formulas (I) and (II). The mole percentages of Formula (I) to Formula (II) can be varied from 0.1 mole % to 99.9 mole %. In one non-limiting embodiment, the molar ratio of Formula (I) to Formula (II) can be 1:99 to 99:1. In another non-limiting embodiment, the molar ratio of Formula (I) to Formula (II) can be 20:80 to 80:20. In yet another non-limiting embodiment, the molar ratio of Formula (I) to Formula (II) can be 40:60 to 60:40.

The hair composition of Formula (I), and/or Formulation (II) can comprise a reaction product of at least one lactone compound and at least one amino alcohol compound. The amino alcohol compound can comprise one, two, three, or more hydroxyl groups.

In one aspect of the present disclosure, the amino alcohol compound can be represented by Formula (III):

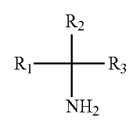

Formula (III)

wherein $R_1$ and $R_2$ each represents an aliphatic hydrocarbon group, an alicyclic hydrocarbon group, an aryl group, or a heterocyclic group, where these groups are substituted with at least one hydroxyl group; and $R_3$ is hydrogen or an alkyl group having 1 to about 12 carbon atoms.

The aliphatic hydrocarbon group used herein can include saturated or unsaturated, liner or branched, substituted or unsubstituted aliphatic hydrocarbon groups. Examples of the aliphatic hydrocarbon groups can include, but are not limited to, a straight or branched alkyl group having 1 to about 12 carbon atoms, such as a methyl group, an ethyl group, a propyl group, an isopropyl group, a butyl group, an isobutyl group, an sec-butyl group, a t-butyl group, a pentyl group, a hexyl group, an octyl group, and a decyl group; an alkenyl group having 1 to 12 carbon atoms, such as a vinyl group, an allyl group, a 1-propenyl group, an isopropenyl group, and a 2-butenyl group; and an alkynyl group having 1 to 12 carbon atoms, such as a 2-propynyl group, and a 2-butynyl group.

The alicyclic hydrocarbon group used herein can include saturated or unsaturated, substituted or unsubstituted alicyclic hydrocarbon groups. Examples of the alicyclic groups can include, but are not limited to, a cycloalkyl group having about 3 to about 10 carbon atoms, such as a cyclobutyl group, a cyclopentyl group, a cyclohexyl group, a cyclooctyl group; and a cycloalkenyl group having about 3 to about 10 carbon atoms, such as a cyclopentenyl group, and a cyclohexenyl group.

The aryl group used herein can comprise about 6 to about 14 carbon atoms, such as a phenyl group, and a naphthyl group.

The heterocyclic group used herein can include those containing at least one hetero atom selected from the group consisting of a nitrogen atom, an oxygen atom, and a sulfur atom. The heterocyclic group may be an aromatic heterocyclic group, a non-aromatic heterocyclic group, or a compound heterocyclic group.

A heterocyclic ring of the above-mentioned heterocyclic group can include a nitrogen-containing heterocyclic ring such as pyrroline, pyrrole, piperidine, piperazine, pyridine, pyrimidine, pyridazine, triazole, and quinoline; an oxygen-containing heterocyclic ring such as tetrahydrofuran, furan, and pyran; a sulfur-containing heterocyclic ring such as tetrahydrothiophene, and thiophene; and a heterocyclic ring containing at least two hetero atoms selected from the group consisting of a nitrogen atom, an oxygen atom, and a sulfur atom, such as thiazoline, thiazolidine, thiazole, thiazine, and morpholine.

In another non-limiting embodiment, the amino alcohol compound can be represented by Formula (IV):

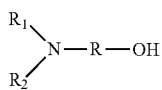

Formula (IV)

where $R_1$ and $R_2$ are independently H, an alkyl group having 1 to about 20 carbon atoms, or an alkyl group having 1 to about 20 carbon atoms substituted with at least one hydroxyl group; and R is an alkyl or alkenyl having about 2 to about 16 carbon atoms.

In yet another non-limiting embodiment, the amino alcohol compound can be represented by Formula (V):

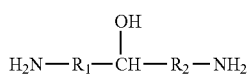

Formula (V)

where $R_1$ and $R_2$ are an alkyl group having 1 to about 20 carbon atoms, or an alkyl group having 1 to about 20 carbon atoms substituted with at least one hydroxyl group.

Examples of the amino alcohol compound can include, but are not limited to, ethanolamine, 2-hydroxyethylhydrazine, 2-methoxyethylamine, 3-amino-1-propanol, amino-2-propanol, 3-amino-1,2-propaediol, serinol, 1,3-diamino-2-propanol, 1-amino-2-methyl-2-propanol, 2-(ethylamino)ethanol, 2-amino-1-butanol, 2-amino-2-methyl-1propanol, 3-methylamino-1-propanol, 4-amino-1-butanol, 2-(2-aminoethoxy)ethanol, 3-methylamino-1,2-propanediol diethanolamine, tris(hydroxymethyl)aminomethane, N-(2-hydroxyethyl)ethylenediamine, meso-1,4-diamino-2,3-butanediol, 2-aminocyclopentanol, 2-(isopropylamino) ethanol, 2-(propylamino)ethanol, 2-amino-3-methyl-1-butanol, 5-amino-1-pentanol, 2-(3-aminopropylamino) ethanol, 1-amino-1-cyclopentanemethanol, 4-aminocyclohexanol, 2-(buty ethanol, 6-amino-1-hexanol, DL-2-amino-1-hexanol, leucinol, N,N'-bis(2-hydroxyethyl)ethylenediamine, 2-aminobenzyl alcohol, 3-aminolbenzyl alcohol, 4-aminobenzyl alcohol, 2-amino-4-methoxyphenol, 3,4-dihydroxybenzylamine, 3,5-dihydroxybenzylamine, 1-aminomethyl-1-cyclohexanol, 2-aminomethyl-1-cyclohexanol N-boc-ethanolamine, 5-amino-2,2-dimethylpentanol, 2-amino-1-phenylethanol, 2-amino-3-methylbenzyl alcohol, 2-amino-5-methylbenzyl alcohol, 2-aminophenylethyl alcohol, 3-amino-2-methylbenzyl alcohol, 3-amino-4-methylbenzyl alcohol, 4-(1-hydroxyethyl)aniline, 4-aminophenethyl alcohol, N-(2-hydroxyethyl)aniline, 3-hydroxy-4-methoxybenzylamine, 3-hydroxytyramine, 6-hydroxydopamine, 4-(Z-amino)-1-butanol, 5-(Z-amino)-1-pentanol, 4-(Z-amino)cyclohexanol, 6-(Z-amino)-1-hexanol, 3-(Boc-amino)-1-propanol, N-Boc-serinol, 2-benzylaminoethanol, 4-(Boo-amino)-1-butanol, 2-(aminomethyl)-2-(hydroxymethyl)-1,3-propanediol, and 2-(2-aminoethyl)-2-(hydroxymethyl)-1,3-propanediol.

The lactone compound of the present disclosure can include, but are not limited to, a cyclic ester compound comprising a heterocyclic ring and the heteroatom on the heterocyclic ring is oxygen, which can be represented by Formula (VI):

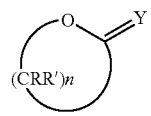

Formula (VI)

wherein R and R' are independently H and a hydrocarbon radical containing from 1 to about 40 carbon atoms that may be saturated or unsaturated, linear or branched, substituted or unsubstituted. The hydrocarbon radicals can comprise hydroxyl groups, amino groups, sulfhydryl groups, aryl groups and halogens. n is an integer of 1 to about 10. Y is oxygen or sulfur. The heterocyclic ring can be saturated or unsaturated.

The lactone compound can comprise 3- to 8-membered rings (including the oxygen on the heterocyclic ring and the carbonyl carbon). Examples of such lactone compounds can include, but are not limited to, α-lactones (3-membered ring alpha-lactones), β-lactones (4-membered ring beta-lactones), γ-lactones (5-membered ring gamma-lactones), δ-lactones (6-membered ring delta-lactones) and ε-lactones (8-membered ring epsilon-lactones).

In one non-limiting embodiment, the lactone compound can be a δ-lactone. In one non-limiting embodiment, the δ-lactone can be represented by Formula (VII):

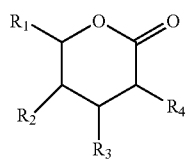

Formula (VII)

wherein $R_1$-$R_4$ are independently H, a hydrocarbon radical having 1 to about 10 carbon atoms, a hydroxyl group, an amino group, a sulfhydryl group, an aryl group, or a halogen.

In one non-limiting embodiment, $R_1$-$R_4$ are independently a hydrocarbon radical being linear or branched, saturated or unsaturated, or substituted or unsubstituted.

Examples of the δ-lactone compounds can include, but are not limited to, meadowfoam δ-lactone, δ-octalactone δ-decalactone, δ-nonalactone, undecanoic δ-lactone, dodecalactone, massoia lactone (or 5-pentylpent-2-en-5-olide), jasmine lactone (or Z-2-pemenylpentan-5-olide), 6-pentyl-alpha-pyrone (or 5-pentylpenta-2,4-lien-5-olide) valerolactone, galactonolactone, glucono δ-lactone, hexadecanolactone, and mevalonolactone.

According to the present disclosure, the lactone compound, the amino alcohol compound, and a solvent can be mixed together at room temperature (~23° C.) to form a mixture. The mixture can then be heated to about 30° C. to about 100° C. for at least 30 minutes to form a reaction product of the present disclosure. In one non-limiting embodiment, the mixture can be heated to about 40° C. to about 80° C. for at least 60 minutes. In another non-limiting embodiment, the mixture can be heated to about 50° C. to about 75° C. for at least 120 minutes. In yet another non-limiting embodiment, the mixture can be heated to about 55° C. to about 65° C. for at least 150 minutes.

The solvent can be water; methanol; acetone; benzene; the other alcohols and/or glycols including but not limited to ethanol, isopropanol (IPA), tert-butyl alcohol (TBA), glycol, ethylene glycol, propylene glycol, diethylene glycol, and dipropylene glycol; and mixtures thereof. In one non-limiting embodiment, the solvent is water. In another non-limiting embodiment, the solvent is methanol. In yet another embodiment, the solvent is a mixture of water with methanol, ethanol, or isopropanol.

The appropriate amounts of the lactone compound and the amino alcohol compound can be determined by a skilled artisan. In one non-limiting embodiment, the molar ratio of the lactone compound to the amino alcohol compound ranges from about 10:1 to about 1:10. In another non-limiting embodiment, the molar ratio of the lactone compound to the amino alcohol compound ranges from about 8:1 to about 1:8. In yet another non-limiting embodiment, the molar ratio of the lactone compound to the amino alcohol compound ranges from about 5:1 to about 1:5. In yet another non-limiting embodiment, the molar ratio of the lactone compound to the amino alcohol compound ranges from about 2:1 to about 1:2.

The hair composition hereinafter can further comprise a sufficient quantity of a buffer system to adjust a pH to about 2 to about 6. The buffer system can be any combination of an acid and a base. Typically, the buffer system comprises an inorganic and/or an organic acid and/or a salt thereof to provide the hair composition with a pH value from about 2 to about 6 at 25° C. In one non-limiting embodiment, the pH value can range from about 3 to about 5. In another non-limiting embodiment, the pH value can range from about 3 to about 4.

In one aspect of the buffering system, the inorganic acid is selected from the group consisting of hydrogen chloride (HCl), sulfuric acid ($H_2SO_4$), nitric acid ($HNO_3$), phosphoric acid ($H_3PO_4$), and combinations thereof.

In another aspect of the buffering system, the organic acid is selected from the group consisting of an alpha-hydroxyl acid, a polycarboxylic acid, and combinations thereof. Accordingly, the organic acid has an acidic functional group having a pKa of about 4.5 or less. In one non-limiting embodiment, the organic has a second acidic functional group having a pKa of about 6 or less.

The organic acid may have a molecular weight less than about 500 grams per mole (g/mall). For example, but not by way of limitation, the molecular weight of the organic acid may be from about 90 g/mol to about 400 g/mol, or from about 100 g/mol to about 300 g/mol, or from about 130 g/mol to about 250 g/mol, or from about 150 g/mol to about 200, or about 190 g/mole. In another aspect, the organic acid may be soluble in water in an amount greater than about 0.2 moles per liter (mol/L) at 25° C. For example, but not by way of limitation, the water solubility of the organic acid may be about 0.3 mol/L or more, or about 0.4 mol/L, or more, or about 0.5 mol/L or more.

Examples of the organic acids can include, but are not limited to, lactic acid, citric acid, tartaric acid, gluconolactive acid, pimelic acid, glyoxylic acid, aconitic acid, ethylenediaminetetraacetic acid, L-glutamic acid, malic acid, malonic acid, and combinations thereof.

Examples of the salt of such an inorganic acid and an organic include its alkali metal salts such as the sodium salt and the potassium salt; its ammonium salt; and its alkanolamine salts such as the triethanolamine salt.

The present disclosure is also directed to a kit for bleaching and/or coloring hair. The kit comprises: (a) a first formulation comprising a hair coloring agent or bleaching agent and (b) a second formulation comprising a hair composition. The first formulation and the second formulation are the same as those described previously. The second formulation can be in the form of a liquid, a cream, a lotion, a milk, a mousse, a spray, a gel, a shampoo, or a conditioner. The second formulation can be provided as two or more separate ingredients.

The kit may further contain a shampoo, a conditioner, instructions for use, a developer, a mixing container, an odor eliminator, an applicator, gloves, or their combinations. The odor eliminator can be incorporated into the first and/or second formulation. Alternately, the odor eliminator is present in a suitable container. Some suitable odor eliminators are known to those of ordinary skill in the art.

The present disclosure is also directed to use of a first formulation and a second formulation for bleaching or coloring hair. The first formulation and the second formulation are the same as those described previously.

The following examples illustrate the presently disclosed and/or claimed inventive concept(s), parts and percentages being by weight, unless otherwise indicated. Each example is provided by way of explanation of the presently disclosed and claimed inventive concept(s), not limitation of the presently disclosed and claimed inventive concept(s). In fact, it will be apparent to those skilled in the art that various modifications and variations can be made in the presently disclosed and claimed inventive concept(s) without departing from the scope or spirit of the invention. For instance, features illustrated or described as part of one embodiment, can be used on another embodiment to yield a still further embodiment. Thus, it is intended that the presently disclosed and claimed inventive concept(s) covers such modifications and variations as come within the scope of the appended claims and their equivalents.

EXAMPLES

Preparation of Products

Example 1—Reaction of GDL with Ethanolamine in Water 6.16 g ethanolamine (EA), 15 g water and 17.9 g L-gluconic acid delta-lactone were sequentially added into a 3-neck flask to form a mixture. Under nitrogen, the mixture was gradually heated to about 60° C. and kept at that temperature for about 2.5 hours. Then, the temperature was decreased to 50° C. and the formed end product was poured into a container. Once the temperature was lowered to room temperature (~21-23° C.), the end product was obtained.

Example 2—Reaction of GDL with 3-Amino-1-propanol in Water 50 g water, ⅓ of the 35.6 g L-gluconic acid delta-lactone (lactone) and 15.0 g 3-amino-1-propanol (APA) were sequentially added into a 3-neck flask to form a mixture. Then the rest of the lactone was added into the mixture. Under nitrogen, the mixture was gradually heated to about 75° C. and kept at that temperature for about 1.0 hour. Then, the temperature was decreased to 50° C. and the formed end product was poured into a container. Once the temperature was lowered to room temperature (~21-23° C.), the end product was obtained.

Example 3—Reaction of GDL with 3-Amino-1-propanol in Methanol 5.0 g (0.2 moles) 3-amino-1-propanol, 200 g methanol and 35.6 g (0.2 moles) L-gluconic acid delta-lactone (GDL) were sequentially added into a 3-neck flask. The mixture was gradually heated under nitrogen to reflux at 60° C. and kept at that temperature for about 2.5 hours. The reaction was allowed to cool to ambient temperature (~21-23° C.). The reaction mixture was filtered and the product was dried in a ventilated oven at 60° C. to give a gluconamide as a white powder.

Example 4—Reaction of GDL with Tris(hydroxymethyl)aminomethane in Methanol 54.0 g L-gluconic acid delta-lactone, 18.3 g ethanolamine and 300 g methanol were sequentially added into a 3-neck flask to form a mixture. Under nitrogen, the mixture was gradually heated to reflux and kept at that temperature for about 2.5 hours. Then, the temperature was decreased to room temperature (~21-23° C.). The final product was filtered and dried. The white powder product was obtained.

Example 5—Reaction of GDL with Tris(hydroxymethyl)aminomethane in Water 50.0 g L-gluconic acid delta-lactone, 34.0 g tris(hydroxymethyl)aminomethane (THMAM) and 70.2 g water were sequentially added into a 3-neck flask to form a mixture. Under nitrogen, the mixture was gradually heated to about 75° C. and kept at that temperature for about 2.0 hours. Then, the temperature was decreased to 50° C. and the formed end product was poured into a container. The end product containing 55 wt % of solids in water was obtained.

Application of the Products

Virgin dark Caucasian hair was used (commercially available from International Hair Importers, Glendale, N.Y., USA) for hair treatment and testing. The products prepared in the Examples described previously were used as additives in hair bleaching and/or coloring treatment. A commercial hair bleaching product (Hair Bleaching Lockblond, containing Lockblond bleaching powder and oxidative crème 12%) was used for bleaching hair. Commercial hair coloring products of Schwarzkopf Brillance Intensive Color Crème 872 (Color 872), Color Wella 5/5 Koleston (Color Wella 5/5), and Majirel IONÈNE G incell L'Oréal professional Paris (Color Majirel) were used for coloring hair. All of the commercial color products contained color crème and oxidative crème. Deionized water or a commercial hair treatment product of Olaplex No. 1 Bond Multiplier (Olaplex No. 1, pH≈3.5) was used as an additive for comparison. Hair bleaching and/or coloring were carried out according to the procedures described as follows:

Bleaching Procedure
  Adding, 2 g of bleach powder, 4 g of oxidative crème, and 1 g of additive into a beaker;
  Mixing all the ingredients using a plastic brush to form a mixture in the beaker;
  Laying a hair switch on an aluminum foil;
  Applying the mixture fully on both sides, from root to tip of the hair switch;
  Wrapping the aluminum foil;
  Processing for about 35 minutes (applying and waiting time);
  Rinsing the hair switch under running water (at about 37° C. and 4 ml/min) for about 5 minutes; and
  Drying the hair switch at about 22° C. overnight.

Coloring Procedure
  Adding 3 g of color crème, 3 g of oxidative crème, and 1 g of an additive into a beaker;
  Mixing all the ingredients using a plastic brush to form a mixture in the beaker;
  Laying a hair switch on an aluminum foil;
  Applying the mixture on both sides from root to tip of the hair switch;
  Wrapping the aluminum foil;
  Processing for about 35 minutes (applying and waiting time);
  Rinsing the hair switch under running water (at about 37° C. and 4 ml/min) for about 5 minutes; and
  Drying the hair switch at about 22° C. overnight.

FT-IR Damage Assessment

Damage caused to the hair was assessed by the FT-IR (Fourier Transform Infrared) method, which has been established to be suitable for studying the effects of oxidative treatments on hair, as shown in Strassburger, J., *J. Soc. Cosmet. Chem.*, 36, 61-74 (1985); Joy, M. & Lewis, D. M., *Int. J. Cosmet. Sci.*, 13, 249-261 (1991); Signori, V. & Lewis, D. M., *Int. J. Cosmet. Sci.*, 19, 1-13 (1997); and Ha, Byung-Jo, *J. Fashion Business*, Vol. 12, No. 6, 23-33 (2008), each publication of which is herein incorporated in its entirety by reference. In particular, these authors have shown that the method is suitable for quantifying the amount of cysteic acid that is produced from the oxidation of cystine. In general, the damage of hair protein proceeds via oxidation of cystine following S—S scission, which yields to cysteric acid. The measurement of cysteic acid units (cysteric acid S=O band intensity) by FT-IR is commonly used to directly estimate the damage to hair by the increase of the S=O band as a result of oxidation of the S—S link in cystine.

It has been found that FT-IR using a diamond Attenuated Total Reflectance (ATR) cell is a sensitive and reproducible way of measuring the cysteic acid content of a single fiber and bundles. This technique is more suitable than using the FT-IR method in simple transmission or microscope modes. The diamond cell ATR is significantly more sensitive and reproducible than the ZnSE cell. Hence, the method used in the present disclosure to measure the cysteic acid content of multiple fiber bundles and full hair switches, is based upon the FTIR diamond cell ATR method employed by Signori and Lewis (1997).

A ratio of 1041 cm$^{-1}$/1076 cm$^{-1}$ peak height values obtained in FT-IR spectrum is used to measure the hair damage in the present disclosure. 1041 cm$^{-1}$ band is generated by the symmetric S=O stretch in cysteric acid. 1076 cm$^{-1}$ corresponds to cystine monoxide. The higher the ratio is; the more damages the hair has.

An IRTracer-100 Fourier Transform Infrared Spectrophotometer equipped with a MiRacle 10 accessory (diamond crystal), commercially available from Shimadzu Corporation, Kyoto, Japan, was used. The spectra were taken from 700-2000 cm$^{-1}$ for 20 scans at the resolution of 4 cm$^{-1}$.

The virgin dark Caucasian hair was bleached for zero, once, twice, and three times, respectively, according to the Bleaching Procedure. The ATR-FTIR scan was conducted at the middle of each hair switch using Swivel sample clamp tips. A calibration curve was obtained by plotting peak height ratios of 1041 cm$^{-1}$/1076 cm$^{-1}$ for zero, once, twice and three times bleached hair versus zero, once, twice and three bleaching times. FIG. 1 shows the resultant correspondent calibration curve. The equivalent damage factor (EDF) for a treated hair by coloring and/or bleaching was calculated based on the calibration curve and the measured ratio of 1041 cm$^{-1}$/1076 cm$^{-1}$.

Hunter Lab Color Measurement

A HunterLab ColorQuest XE Spectrophotometer (commercially available from Elscolab B.V., The Netherlands) was used to measure visually color scale from a hair sample by using reflected light between 400 and 700 nm. The hair sample was inserted into the grooved area of the special port plate, and was measured 5 times at one side along the whole hair tress, and repeated 5 times at another side. For a hair sample under bleaching treatment, a Lightness (L-scale) was measured. For a hair sample under coloring treatment, the color tonality changing after the treatment was measured by using a, and b-scale as shown below.

(Lightness) axis—0 for black, 100 for white, and 50 for middle grey.
(Red-green) axis—positive values for red, negative values for green, and 0 for neutral.
(Blue-yellow) axis—positive values for yellow, negative values for blue, and 0 for neutral.

Dry Friction Measurement:

Dry Friction of a hair sample was measured using an MTT175 instrument fitted with a dry friction accessory (commercially available from Diastron-limited UK, Hampshire, UK). A 10" long of 5 g hair switch was mounted both sides onto a flat plate (friction plate) and a clean rubber probe was used (for each measurement). The middle part of the hair switch was taken for measurement. The plate was moved forward 40 mm and backward 40 mm while a load cell measured the force during the displacement at 150 mm/minute on both sides of each hair switch. A constant vertical force 400 g was applied onto the weight post. The average friction force between the selected region of 25-60 mm, and between the hair substrate and rubber was divided by the applied vertical force to calculate the coefficient of friction (also called the work done energy). In the present disclosure, the dry friction is expressed in Joule using the work required to displace outward the rubber probe along the hair (also called the work done outward energy). Outward displacement was meant with the hair cuticle direction or from root to tip part of hair switch. The lower the work done outward energy is, the smoother the hair has.

Example 6

Virgin dark Caucasian hair was treated and tested. Tables 1-5 list the hair treatment and testing results using various additives. The pH of the sample prepared in Example 2 was adjusted to about 5.3 by adding DL-tartaric acid before using as an additive in the hair treatment.

In Table 1, the virgin dark Caucasian hair was first bleached once without using an additive based on the Bleaching Procedure described previously. The bleached hair was then bleached again with an additive based on the Bleaching Procedure. The EDF and Lightness (L) after the treatment were measured.

TABLE 1

| Sample | EDF | Lightness (L) |
| --- | --- | --- |
| 1x Bleached, starting point | 1.10 | 30 |
| Extra bleached, added water | 1.54 | 42 |
| Extra bleached, added Olaplex No. 1 | 1.35 | 40 |
| Extra bleached, added Sample of Example 2 | 1.42 | 41 |

In Table 2, the virgin dark Caucasian hair was bleached three times with an additive based on the Bleaching Procedure except 60 minutes were used for processing. The Dry Friction and Lightness after the treatment were measured.

TABLE 2

| Sample | EDF | Dry Friction (J) | Lightness (L) |
| --- | --- | --- | --- |
| Caucasian virgin, starting point | 0.00 | 0.100 | 21 |
| 3x Bleached, added water | 2.55 | 0.128 | 59 |
| 3x Bleached, added Olaplex No. 1 | 1.75 | 0.121 | 55 |
| 3x Bleached, added Sample of Example 2 | 2.23 | 0.118 | 58 |

Tables 3-5 list the color treatment and testing results using commercial color product Color 872, Color Wella 5/5 and Color Majirel, respectively. First, the virgin hair was bleached once without using an additive based on the Bleaching Procure. Then the bleached hair was colored using the commercial color products along with the additive based on the Coloring Procedure described previously except for 2 minutes rinsing time for Color Majirel. The EDF, Dry Friction and Redness were measured.

TABLE 3

| Sample | EDF | Dry Friction (J) |
| --- | --- | --- |
| 1x Bleached, starting point | 1.00 | — |
| Color 872, added water | 1.17 | 0.085 |
| Color 872, added Olaplex No. 1 | 0.91 | 0.091 |
| Color 872, added Sample of Example 2 | 0.89 | 0.062 |

TABLE 4

| Sample | EDF | Redness (a) |
| --- | --- | --- |
| 1xBleached, staring point | 0.99 | — |
| Color Wella 5/5, added water | 1.02 | 6.3 |
| Color Wella 5/5, added Olaplex No. 1 | 0.94 | 6.6 |
| Color Wella 5/5, added sample of Example 2 | 0.92 | 6.6 |

TABLE 5

| Sample | EDF | Dry Friction (J) | Redness (a) |
| --- | --- | --- | --- |
| Caucasian virgin, starting point | 0.00 | 0.080 | 2.8 |
| Color Majirel, added water | 0.22 | 0.089 | 5.3 |

TABLE 5-continued

| Sample | EDF | Dry Friction (J) | Redness (a) |
|---|---|---|---|
| Color Majirel, added Olaplex No. 1 | 0.14 | 0.075 | 4.7 |
| Color Majirel, added Sample of Example 2 | 0.16 | 0.066 | 5.4 |

The experimental results clearly show that the hair composition of the present disclosure can reduce the damages caused by coloring and/or bleaching.

What is claimed is:

1. A method for coloring or bleaching hair comprising steps of:
   (a) applying a first formulation comprising a hair coloring agent or bleaching agent to the hair; and
   (b) applying to the hair a second formulation comprising a hair composition comprising a reaction product of L-gluconic acid delta lactone and ethanol amine and water, wherein the reaction represented by one or both of the following formulas:

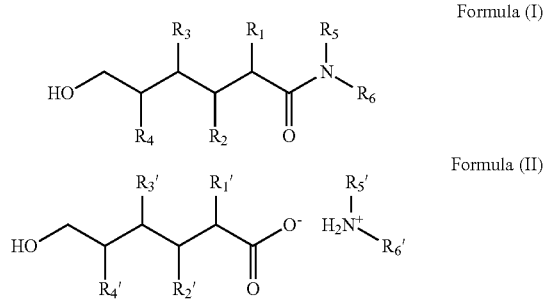

Formula (I)

Formula (II)

wherein $R_1$-$R_5$ and $R_1'$-$R_4'$ are hydrogen and $R_6$ and $R_6'$ are —CH2-CH2-OH.

2. The method of claim 1, wherein the steps (a) and (b) are performed simultaneously.

3. The method of claim 1, wherein the second formulation further comprises one or more pharmaceutical excipients selected from water, surfactants, vitamins, natural extracts, preservatives, chelating agents, perfumes, preservatives, antioxidants, proteins, amino acids, humectants, fragrances, emollients, penetrants, thickeners, viscosity modifiers, hair fixatives, film formers, emulsifiers, opacifying agents, propellants, liquid vehicles, carriers, salts, pH adjusting agents, neutralizing agents, buffers, hair conditioning agents, antistatic agents, anti-frizz agents, anti-dandruff agents, and combinations thereof.

4. The method of claim 3, wherein the pharmaceutical excipient is present in an amount ranging from about 10 wt % to about 99 wt % of the second formulation.

5. The method of claim 1, wherein the second formulation is in the form of a gel, cream, shampoo, or conditioner.

6. The method of claim 1, wherein the step (b) is repeated one or more times.

7. The method of claim 1, further comprising: rinsing, shampooing, or conditioning the hair, which is step (c) wherein the step (c) occurs subsequent to the step (b).

8. The method of claim 7, wherein the step (c) is performed within about 10 seconds to about 30 minutes after the step (b).

9. The method of claim 1, wherein the hair coloring agent is selected from the group consisting of highlighting agents, permanent coloring agents, demi-permanent coloring agents, and semi-permanent coloring agents.

* * * * *